United States Patent [19]

Poormon

[11] Patent Number: 5,005,423

[45] Date of Patent: Apr. 9, 1991

[54] CRACK GROWTH RATE MEASURING INSTRUMENT

[75] Inventor: Mark L. Poormon, Palm City, Fla.

[73] Assignee: United Technologies Corporation, Hartford, Conn.

[21] Appl. No.: 582,812

[22] Filed: Sep. 13, 1990

[51] Int. Cl.⁵ ............................................. G01N 19/08
[52] U.S. Cl. ...................................................... 73/799
[58] Field of Search .......... 73/799, 811, 812, 849–854, 73/856, 860, 799

[56] References Cited

U.S. PATENT DOCUMENTS 3,138,016  6/1964  Orner ..................................... 73/799
3,323,356  6/1967  Arias ..................................... 73/852

FOREIGN PATENT DOCUMENTS 1374093  2/1988  U.S.S.R. ................................. 73/849

OTHER PUBLICATIONS

Hoffelner, "Fatigue Crack Growth at 20 kHz-A New Technique", J. Phy. E.: Sci. Instrum., vol. 13, No. 6, Jun. 1980, pp. 617–619.

Primary Examiner—Robert Raevis
Attorney, Agent, or Firm—Norman Friedland

[57] ABSTRACT

A fatigue crack growth rate measuring instrument serves to screen specimens of materials by cycling of load at a constant displacement and recording the load v cycle characteristics and calculating the da/dN v. Δ K for ascertaining if the specimen falls within or without the range of acceptability.

5 Claims, 3 Drawing Sheets

CRACK GROWTH RATE MEASURING INSTRUMENT

This is a continuation of Ser. No. 423,926 (now abandoned).

TECHNICAL FIELD

This invention relates to testing equipment for measuring fatigue crack growth rates of notched specimens and particularly for test apparatus for applying a constant displacement cyclically to the 3-point-bend notched specimen for screening purposes.

BACKGROUND ART

The typical test for measuring the crack growth rate of a notched specimen tested in accordance with ASTM test method E647-88, volume 03.01 of the 1988 ASTM Standards requires a significant amount of time with the use of costly testing equipment. Materials typically used in aircraft engines usually require two to three weeks or longer to perform the 3-point-bend specimen crack growth test. Obviously, in the development process of new alloys, it would be an advantage to be able to screen the new alloys over a shorter period of time using less costly test machinery.

I have found that I can obtain an indication of whether or not a specimen has the likelihood of meeting success by subjecting the specimen to a constant load either under the temperatures in which the material is intended for ultimate use or under standard day or ambient conditions. The test equipment consists of a relatively inexpensive fixture, motor driven eccentric for cyclically displacing a load over a constant distance and recording the load level with a standard 4 arm bridge load cell. This allows one to ascertain and calculate a single point of the $\Delta K$ (stress intensity) and compare the results with the stress-intensity factor range versus the crack growth rate (da/dn) which is indicative of the material's resistance to stable crack extension under cyclic loading.

This type of screening that discounts the specimens that are unlikely to succeed saves time, and would allow better utilization of the more expensive equipment for standardized 3-point crack growth testing would realized.

Furthermore, it is contemplated that this testing equipment could be operated by personnel without having to expend a great amount of training.

SUMMARY OF THE INVENTION

An object of this invention is to provide means for screening test specimens to ascertain the likelihood of success in a 3-point-bend crack growth evaluation. A constant displacement is applied to the specimen at 3-points to ascertain a single point in the $\Delta K$ for a given crack growth rate. The test equipment is characterized as being relatively simple, inexpensive and easy to operate.

The foregoing and other features and advantages of the present invention will become more apparent from the following description and accompanying drawings

BEST MODE FOR CARRYING OUT THE INVENTION

Figure 1:
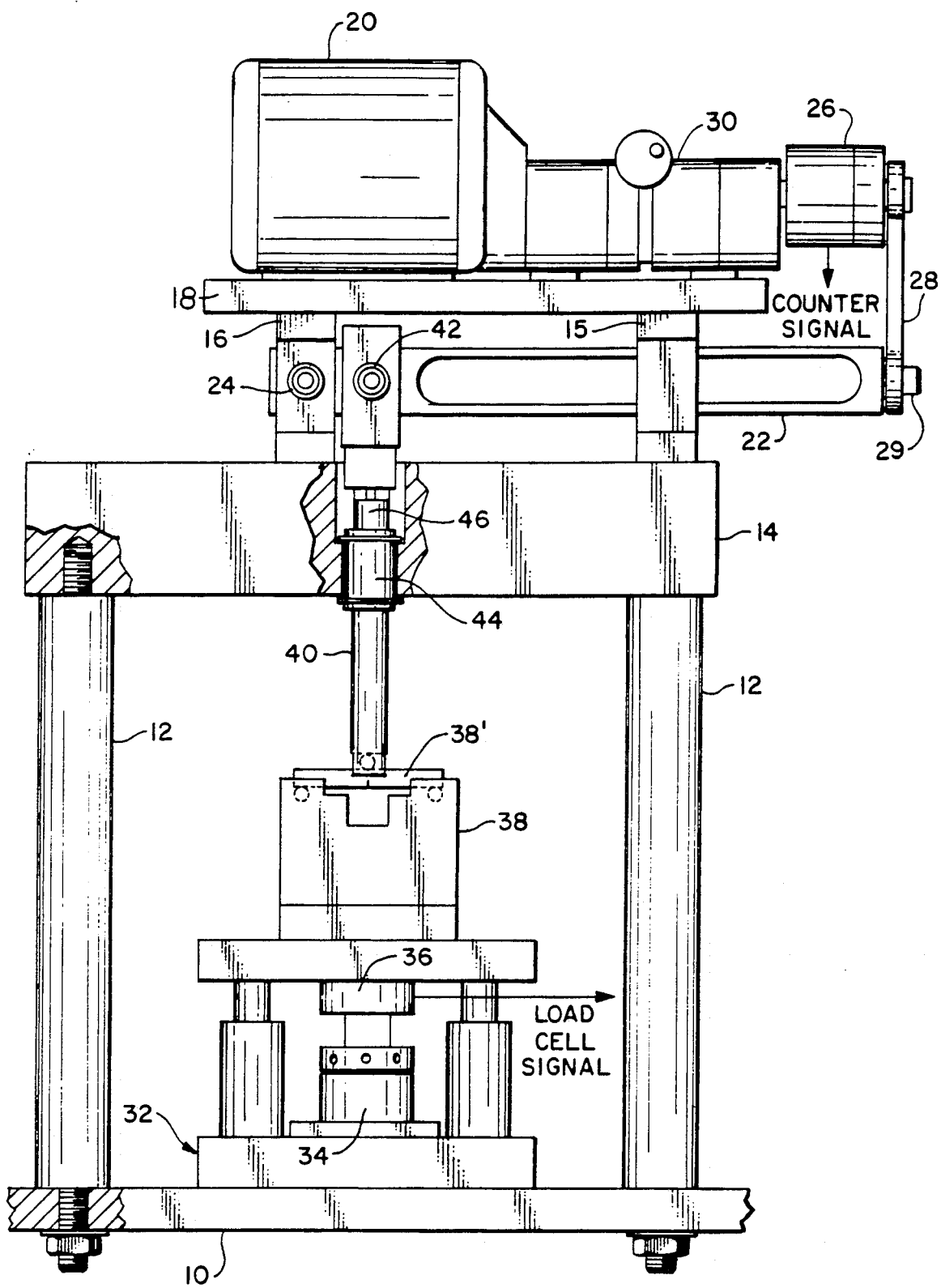
FIG. 1 is an elevated front view of the invention.

As contrasted from the standard 3-point fatigue crack growth rate tests this invention contemplates applying a constant displacement cycle rather than the constant load cycle in the standard test. The equipment utilized in the testing machine is commercially available and the details thereof is omitted herefrom for the sake of convenience and simplicity. As shown in FIG. 1, the test equipment includes support structure including a suitable table 10 having support columns 12 supporting a cross head 14. Bifurcated supports 15 and 16, in turn, are mounted on cross head 14 and support the platen 18 which supports a suitable electrically driven motor 20. Fulcum lever 22 is pivotally mounted between the arms of bifurcated supports 15 & 16 by a suitable pivot 24 supported in support 16. The other end of fulcum lever 22 is connected to an eccentric crank 26 via the connecting rod 28 by a spherical bearing 29.

A suitable gear head drive 30 interconnects the motor 20 to the eccentric crank 26 to cause the lever arm to be displaced vertically. A precision die set 32 rests on table !0 and supports the jack screw assembly 34. The jack screw assembly 34 serves to preload the commercially available load cell 36 which, in turn, is connected to the specimen adapter 38 that holds the specimen being tested, as represented by specimen 38'.

The load from fulcum lever 22 is applied to the specimen through the load rod 40 which is connected to the fulcum lever 22 by suitable roller bearings and its support 42.

A linear bearing 44 and an alignment coupling 46 may be utilized to assure that the load is accurately directed vertically relative to the load cell.

Figure 2:
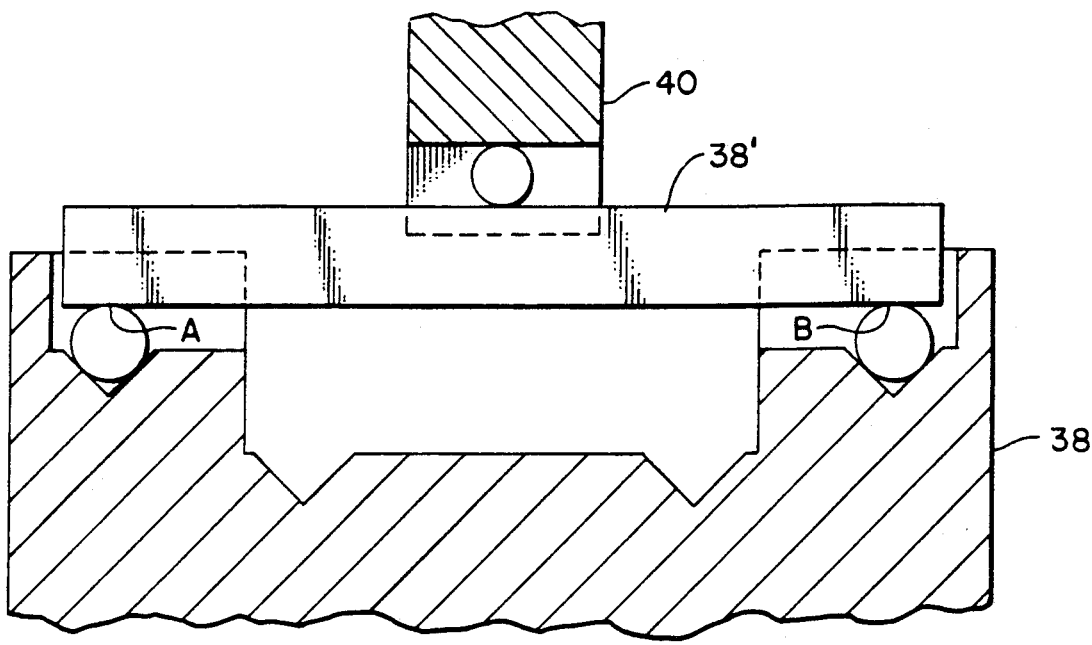
FIG. 2 is a partial view showing a specimen mounted in FIG. 1
Figure 3:
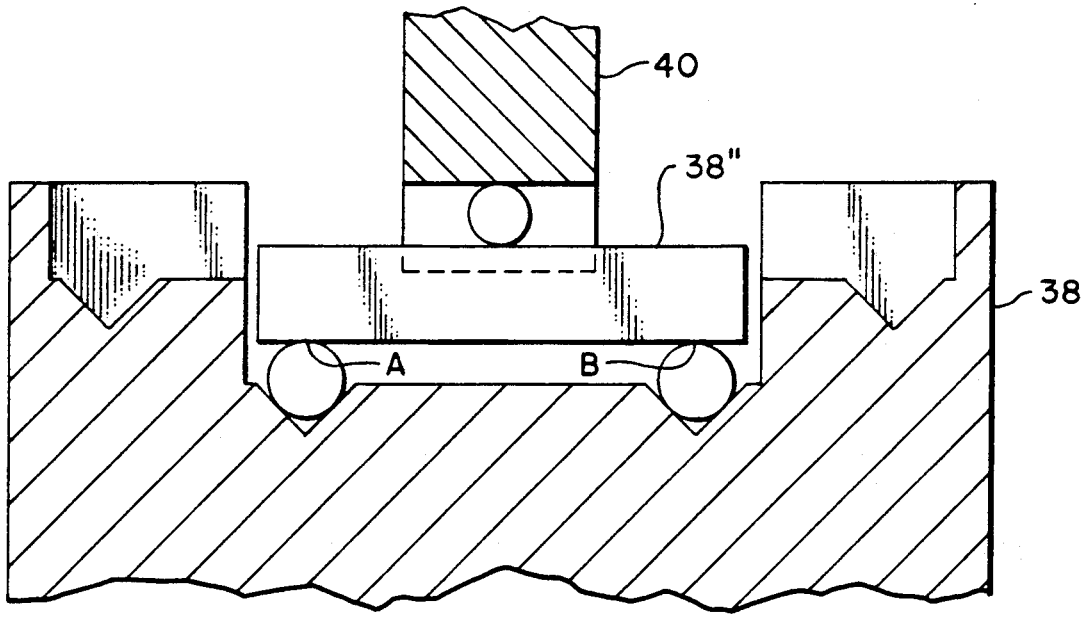
FIG. 3 is a partial view showing a different size specimen similarly mounted in the same adapter.

As noted in FIGS. 2 and 3, different sized specimens 38' and 38" may be used in a single specimen adapter 38.

A load signal from the load cell 36 and a signal counting the revolutions of the eccentric crank 26 are suitably recorded in a well known instrument. For this purpose, a suitable load cell conditioner/indicator may be a DAYTRON model 3270x and a suitable recording instrument with a digital counter may be a Data Acquisition System by FLUKE model number 1752A.

As is apparent from the foregoing either a standard 2 inch or 4 inch specimen may be tested in the constant displacement test rig to perform a 3-point-bend test. In operation, the cyclic load is applied to the center of the notched specimen suitably supported at two points A and B by the adapter 34. Preloading is initially applied via the jack screw assembly 34 to comply with the stress-ratio (minimum stress/maximum stress) requirements test a specific stress ratio. By virtue of the alignment coupler 46, linear bearing 44 and the combined die set 32 and adapter 34 precise 3-point loading is attainable. The counter is a suitable micro-switch/cam arrangement that detects the number of cycles and triggers a mechanical totalizer. The in-line load transducer of the load cell 36, as noted above, relays the load signal through the signal conditioner/indicator. The load value applied to the specimen may be displayed on a digital panel meter in engineering units.

Figure 4:
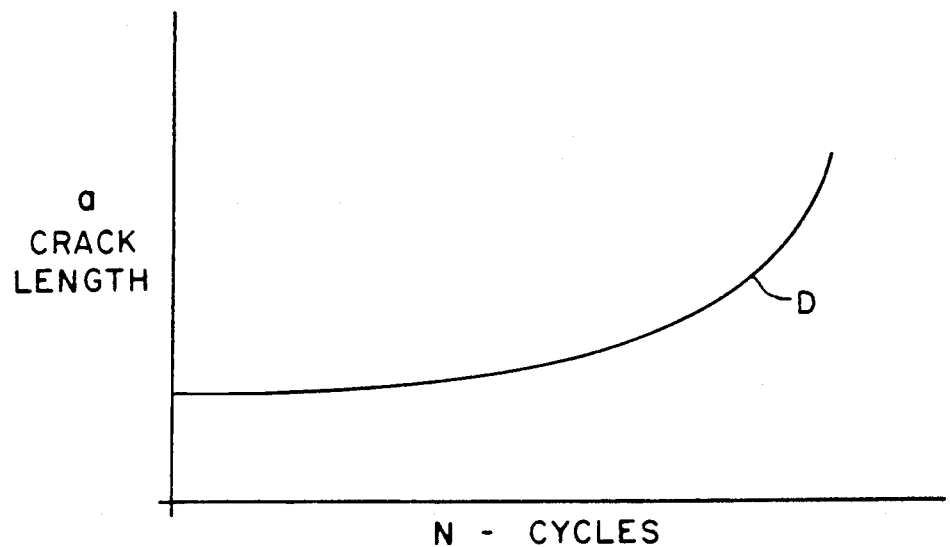
FIG. 4 is a graph showing the relationship of a crack relative to the number of test cycles of a specimen.

The measurements obtained during the test and can be plotted as shown in FIG. 4 where the ordinate a is the crack length and the ordinate N is the cycles which forms curve D. The a is obtained by a visual measurement and its others are read off of the mechanical counter.

Figure 5:
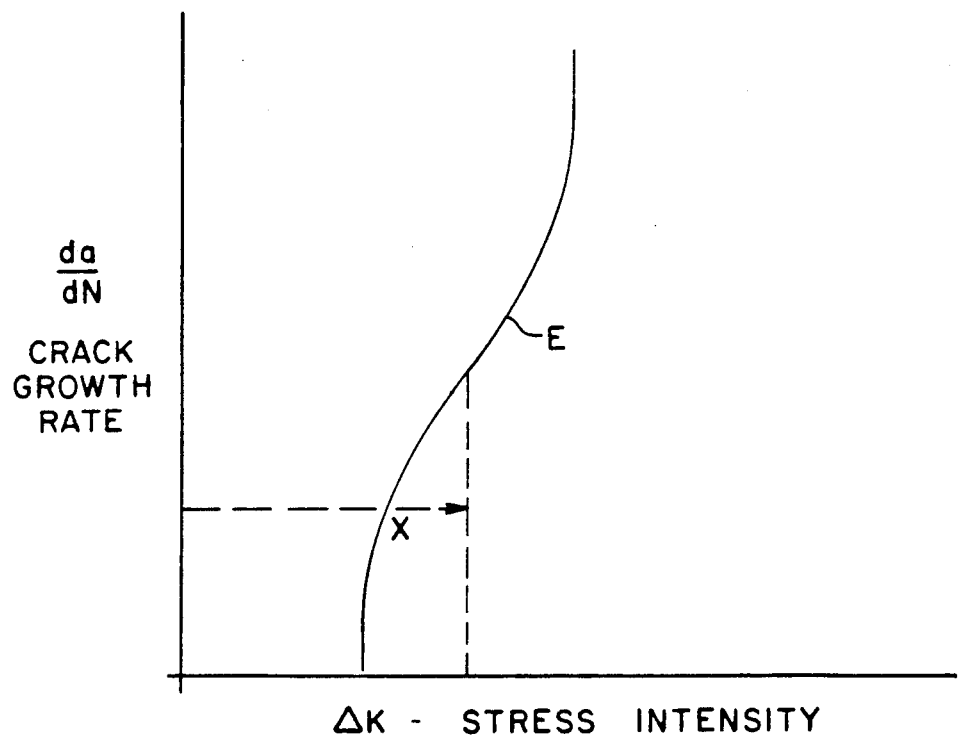
FIG. 5 is a graph plotting da/dN v.$\Delta K$ illustrating the results of the test in FIG. 4.

The plot in FIG. 5 are calculated values of these measured signals where the differential da/dN (crack growth rate) is measured against ΔK, where ΔK is the stress intensity which is a well-known function of crack length a, σ and g where σ is the measured stress and g is a constant based on the geometry of the test machine.

The curve E represents baseline fatigue crack growth rate of a given material which is the datum used in making the comparison and the point X is the test results of the specimen. Had X fallen to the left of curve E, the specimen would have failed the test and further testing and hence developing of this alloy would be unwarranted. Being that it falls to the right of curve E further testing of this alloy is justified According to this invention it is readily apparent that the operating controls and calibration adjustments are easily accessible and complete rig assembly and disassembly can be accomplished expeditiously. The test machine is characterized by its low construction cost (most of the parts are commercially available), simplicity of operation and inherent failsafe features.

Test specimens cannot be accidentally overloaded due to electrical or hydraulic power loss. In addition, the machine is not susceptible to stray RF noise or line voltage spikes as is common with conventional equipment using reactive-type transducers (LVDT). Elevated temperature tests can be run on this machine as temperature sensitive components (i.e., load cell, linear bearing, etc.) are either assembled away from hot zone or have provisions made for adequate cooling. Also, as previously mentioned, precise point loading alignment can be repeatedly achieved as a result of an innovative unified load-train design. This, coupled with a rigid lever arm arrangement, will provide accurate and continuous duty testing.

Although this invention has been shown and described with respect to detailed embodiments thereof, it will be understood by those skilled in the art that various changes in form and detail thereof may be made without departing from the spirit and scope of the claimed invention.

What is claimed is:

1. Test apparatus for screening alloys dimensioned in a prescribed notched specimen to ascertain a specific ratio of the crack growth rate to a given stress intensity comprising a horizontal table, vertical support columns, a cross head horizontally supported to said support columns, a platen supported horizontally by said cross head, a die set supported on said table underlying said platen, a motor supported to said platen, an eccentric driven by said motor, a fulcrum lever supported to said cross head being pivoted at one end and driven by said eccentric on the other end, a load rod interconnected to said fulcrum lever and bearing against said notched specimen, an adapter holding said notched specimen in a predetermined spacial relationship, and said adapter being supported to said die set and being in cooperating relationship with a load cell, means for imparting movement from said motor for driving said eccentric and load rod to cyclically apply a constant displacement to said notched specimen and means for recording the cycles of said eccentric varying load imposed on said load cell whereby the differential of the crack length and cycles (da/dN) can be calculated and plotted against the stress intensity (ΔK) to obtain a single point to be compared with a base line curve indicative of a given da/dN v.ΔK and where the load will seek its own value.

2. Test apparatus as claimed in claim 1 including a gear head drive is interconnecting said motor and said eccentric.

3. Test apparatus as claimed in claim 2 including roller bearing means supporting said load rod to said fulcrum lever.

4. Test apparatus as claimed in claim 3 including a linear bearing and an alignment couple supporting said load rod to said cross head.

5. Test apparatus as claimed in claim 4 wherein said adapter has holding means for supporting different sized specimens.

* * * * *

UNITED STATES PATENT AND TRADEMARK OFFICE
CERTIFICATE OF CORRECTION

PATENT NO. : 5,005,423

DATED : April 9, 1991

INVENTOR(S) : Mark L. Poormon

It is certified that error appears in the above-identified patent and that said Letters Patent is hereby corrected as shown below:

On the title page:

Element [57], line 2: "cycling of" should read --cycling a--

Col. 1, line 40: "(da/dn)" should read --(da/dN)--

Col. 1, line 46: after "testing" delete "would realized"

Col. 2:

line 13: after "load cycle" insert --utilized-- line 22: "Fulcum" should read --Fulcrum-- line 24: "fulcum" should read --fulcrum-- line 35: "fulcum" should read --fulcrum--
    line 37: "fulcum" should read --fulcrum--
    line 11, "on" should read --in-- line 24, after "eccentric" insert --and the--

In claim 2, line 32: after "drive" delete "is"

Signed and Sealed this

Second Day of February, 1993

*Attest:*

STEPHEN G. KUNIN

*Attesting Officer*     *Acting Commissioner of Patents and Trademarks*